United States Patent [19]

Horner et al.

[11] 4,268,446
[45] May 19, 1981

[54] PREPARATION OF CHROMANE DERIVATIVES

[75] Inventors: Michael Horner, Neustadt; Axel Nissen, Leimen, both of Fed. Rep. of Germany

[73] Assignee: BASF Aktiengesellschaft, Fed. Rep. of Germany

[21] Appl. No.: 121,170

[22] Filed: Feb. 13, 1980

[30] Foreign Application Priority Data

Mar. 12, 1979 [DE] Fed. Rep. of Germany ....... 2909601

[51] Int. Cl.³ .............................................. C07D 311/58
[52] U.S. Cl. ................................................. 260/345.5
[58] Field of Search ........................... 260/345.2, 345.5

[56] References Cited

U.S. PATENT DOCUMENTS 4,003,919 1/1977 Scott et al. ....................... 260/345.5

Primary Examiner—Nicky Chan
Attorney, Agent, or Firm—Keil & Witherspoon

[57] ABSTRACT

Chromane derivatives (I)

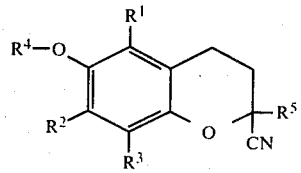

where $R^1$, $R^2$ and $R^3$ are H or $C_1$–$C_8$-alkyl, $R^4$ is H, $C_1$–$C_8$-alkyl or $C_1$–$C_8$-acyl and $R^5$ is $C_1$–$C_8$-alkyl are prepared by reacting a hydroquinone (II)

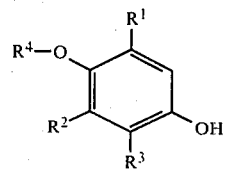

with a Lewis acid or a Lewis acid derivative having the same action, and with a nitrile $CH_2=CH-C(R^5)(OR^6)CN$ (III), where $R^6$ is H, $C_1$–$C_4$-acyl or $C_1$–$C_4$-alkyl, or with a compound from which III is formed in situ, in the presence of an inert solvent.

3 Claims, No Drawings

PREPARATION OF CHROMANE DERIVATIVES

The present invention relates to a novel process for the preparation of chromane derivatives of the general formula I

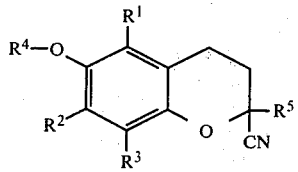

where $R^1$, $R^2$ and $R^3$ are hydrogen or alkyl of 1 to 8 carbon atoms, $R^4$ is hydrogen or alkyl or acyl of 1 to 8 carbon atoms and $R^5$ is alkyl of 1 to 8 carbon atoms.

German Laid-Open Application DOS No. 2,364,141 discloses the preparation of 6-hydroxy-2-cyano-2,5,7,8-tetramethylchromane from trimethylhydroquinone and vinyl methyl ketone in a five-stage synthesis, as shown schematically below

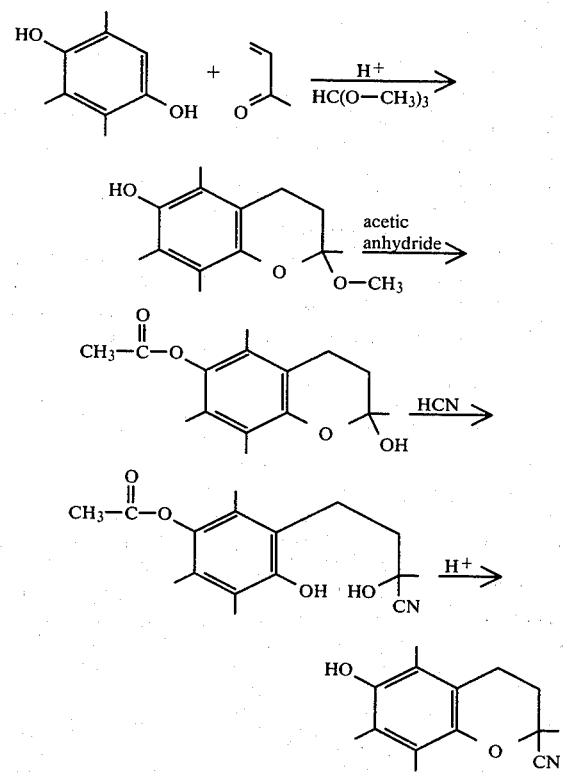

Since this procedure is evidently involved, it is the object of the present invention to make chromane derivatives I, which are well-known to be important for the preparation of antioxidants, more readily accessible.

We have found that this object is achieved and that chromane derivatives of the general formula I

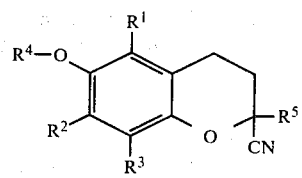

where $R^1$, $R^2$ and $R^3$ are hydrogen or alkyl of 1 to 8 carbon atoms, $R^4$ is hydrogen or alkyl or acyl of 1 to 8 carbon atoms and $R^5$ is alkyl of 1 to 8 carbon atoms are obtained economically in a remarkable one-stage reaction if a hydroquinone of the general formula II

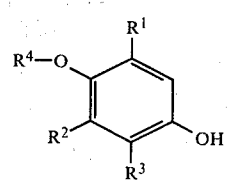

is reacted with 10–300 mole %, based on II, of a Lewis acid or of a Lewis acid adduct with a weak Lewis base or of a Lewis acid adduct with a proton acid, and with a nitrile of the general formula III

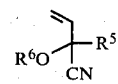

where $R^6$ is hydrogen or acyl or alkyl of 1 to 4 carbon atoms, or with a compound from which III is formed in situ under the reaction conditions, in the presence of an inert solvent.

Preferred starting compounds II, amongst those conforming to the above definition, are those where the sum of the carbon atoms in the alkyl radicals $R^1$, $R^2$ and $R^3$ is from 3 to 10. Compounds of particular importance are trimethylhydroquinone and hydroquinone derivatives where one of the radicals $R^1$, $R^2$ and $R^3$ is a long-chain alkyl and the others are hydrogen or methyl. Further examples of important compounds are hydroquinone, tert.-butylhydroquinone and 2,3- and 2,6-dimethylhydroquinone.

If the starting materials used are hydroquinones II, as defined above, in which the 1-hydroxyl group is protected, ie. etherified or esterified ($R^4 \neq H$), the free 6-hydroxy compound is in every case obtained alongside the corresponding 6-substituted chromane derivatives I. However, the two products are easy to separate because of their different solubility characteristics. The protected hydroquinones are particularly used as starting materials if the 3- and 6-positions of the benzene ring are unsubstituted and bis-addition of III is to be suppressed. Frequently, the 1-hydroxyl group of compound II already carries a protective group, resulting from the method of synthesis; in that case it is not necessary to split off the protective group before carrying out the further reaction. Finally, protection of the 6-hydroxyl groups in I may be advantageous if further reactions are to be carried out with I.

Amongst the starting compounds III according to the definition given, those where $R^5$ is alkyl of 1 to 4 carbon atoms deserve particular mention, and those where $R^5$ is methyl are especially important. These compounds are known or may be obtained by conventional methods.

Instead of the nitriles III, it is possible to employ compounds from which III is formed in situ under the reaction conditions, especially nitriles of the general formula IIIa

where X is halogen, hydroxyl or alkoxy or acyloxy of 1 to 4 carbon atoms.

Since the cyanohydrins (where $R^6$ is H) III and IIIa are in any case formed under weakly acid conditions from a carbonyl compound IIIb or IIIc

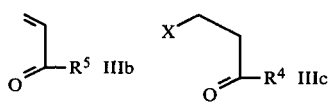

and a cyano compound IV

Y—CN   IV where Y is hydrogen, one equivalent of a metal cation, or a trialkylsilyl group, it is frequently advantageous, in synthesizing I, to start not from III but from an equimolar or about equimolar mixture of IIIb or IIIc and IV, as a result of which the step of separately preparing III or IIIa can be saved.

Furthermore, compounds III are formed from IV and enol-ethers or ketals of the formulae IIId-g

where $R^{5'}$ is an alkylidene corresponding to alkyl $R^5$, and $R^6 \neq H$

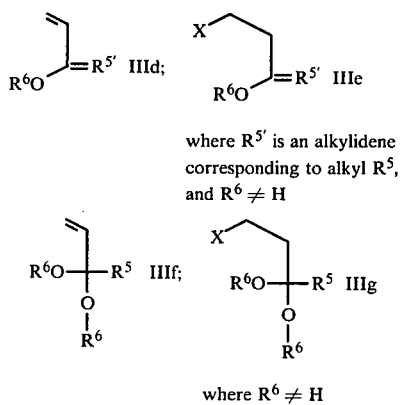

where $R^6 \neq H$

However, from an economic point of view, compounds IIId-g are normally of less importance as starting materials for the process according to the invention.

Compounds of type III and IIIa, where $R^6 \neq H$, are obtainable by conventional methods, for example by alkylating or acylating the free alcohols. Suitable radicals $R^6$ are in particular methyl, ethyl and acetyl.

The starting compounds III, IIIb, IIId and IIIf have in common the vinyl group which is required for an addition reaction with II and which reacts in the manner of a Friedel-Crafts reaction. Hence, a group —CH$_2$—CH$_2$—X, such as is suitable for Friedel-Crafts alkylation reactions, can be present instead of the vinyl group, and accordingly compounds IIIa, IIIe and IIIg can also be used as starting materials. Suitable radicals X are in particular chlorine, bromine, hydroxyl, methoxy and acetoxy.

Amongst the procedures mentioned, the reaction of II with a cyanohydrin III (where $R^6$ is H) is as a rule preferred, because it gives the best yields. On the other hand, the other methods may be advisable if the particular starting compounds are especially easily obtainable.

Preferably, compounds II and III or their precursors are employed in equimolar amounts, but in order to accelerate the reaction it may be advisable to use III in up to 1.2-molar excess. A larger excess as a rule offers no further advantages.

The use of a Lewis acid in order to link III to II is an essential feature of the process according to the invention. The amount of Lewis acid is 10–300, preferably 30–120, mole %, based on II. Where X is hydroxyl, it must be borne in mind that the OH group alone will consume 1 mole of the Lewis acid.

Suitable catalytically active compounds are:

The Lewis acid itself, for example a boron halide such as $BF_3$, $BCl_3$ and $BI_3$, an aluminum halide, such as $AlCl_3$, $AlBr_3$ and $AlI_3$, a tin tetrahalide, such as $SnCl_4$, $SnBr_4$ and $SnI_4$, a zinc halide, such as $ZnCl_2$, $ZnBr_2$ and $ZnI_2$, and iron dihalides;

Adducts of Lewis acids with Lewis bases which are of lower basic strength than the starting compounds II, ie., for example, adducts of the above metal halides with eithers, eg. dimethyl ether, diethyl ether and tetrahydrofuran, with esters, eg. ethyl acetate, with nitriles, eg. acetonitrile and benzonitrile, with lactones, eg. γ-butyrolactone, with nitro compounds, eg. nitromethane and nitrobenzene, and with ketones, eg. acetone and acetophenone. The use of these adducts has the advantage of facilitating handling, since, because of their solubility in organic media, the adducts can be metered more easily; furthermore, the adducts in most cases make it possible to carry out the process in a homogeneous phase from the very start;

Adducts of Lewis acids with proton acids, for example with mineral acids, eg. phosphoric acid, sulfuric acid and hydrochloric acid. These adducts, which can be formulated as complex acids of the following type $$HCl + BCl_3 \rightleftharpoons H[BCl_4]$$

frequently accelerate the reaction according to the invention more strongly than do the Lewis acids on which they are based.

Amongst the Lewis acids, boron trifluoride and boron trifluoride diethyl-etherate are preferred.

Suitable inert solvents are, in general terms, aprotic fluids having a donicity of at most 20. The term donicity is defined in a paper by V. Gutmann, Angew. Chem. 82 (1972), 858. It expresses the affinity for Lewis acids and means, in the present instance, that the solvent should not form a stable adduct with the Lewis acids. Accordingly, examples of suitable solvents are methylene chloride, 1,2-dichloroethane, chloroform, benzene, toluene, chlorobenzene, nitromethane, nitrobenzene, benzonitrile, acetonitrile, cyclohexane and mixtures of these solvents.

Amongst the above solvents, mixtures of toluene or methylene chloride with nitromethane are particularly suitable. The function of the solvents is to ensure that at least a proportion of the reactants employed remains in homogeneous solution. The amount of solvent can vary within wide limits but is in general from 1 to 10 kg per kg of II.

The reaction temperatures are preferably from −50° C. to 100° C., especially from −40° C. to 60° C. Since the reaction can under certain circumstances take place very vigorously, which can lead to increased formation of undesirable products, it is advisable to start the reaction at a low temperature and then gradually to raise the latter. Too vigorous a reaction can also be avoided by adding the reactants gradually.

Since the reaction can be carried out under atmospheric pressure, there is as a rule no reason to use reduced to superatmospheric pressure.

There is no need to conform to any other special technical conditions, ie. the reaction can be carried out conventional preparative techniques, for example by mixing a solution of III, or of a precursor of III, with IV and adding gradually and simultaneously a solution of II and the Lewis acid or a solution of the Lewis acid or one of the Lewis acid adducts mentioned. Since certain cyanohydrins III are slightly unstable, they can be stabilized with a small amount of acid, for example phosphoric acid.

The reaction mixtures can be worked up by the conventional methods for Friedel-Crafts reactions, for example by adding water, with or without ether, to the mixture and distilling the solvents from the dried organic phase. The crude product thus obtained, which contains about 70-90% yield of I, can, if desired, be purified by recrystallization, for example from acetone/water.

A compound I can be converted by hydrolysis, in a conventional manner, to the chromane-carboxylic acid V

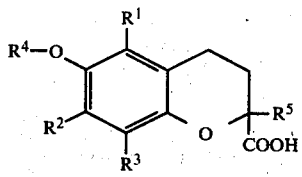

The compounds V, and especially 6-hydroxy-2,5,7,8-tetramethylchromane-2-carboxylic acid Va

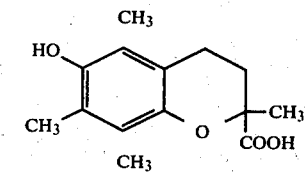

are well-known important antioxidants for organic materials, such as fats and oils, and for pharmaceutical and cosmetic formulations.

Example 1

A suspension of 180 g of toluene, 51.4 g (0.338 mole) of trimethylhydroquinone and 23.0 g (0.338 mole) of $BF_3$ was added in the course of one hour, under a nitrogen atmosphere, to a solution of 33.6 g (0.338 mole) of methyl vinyl ketone cyanohydrin (mixed with 1.3 g of phosphoric acid as a stabilizer), 63 g of toluene and 34 g of nitromethane, at 0°–5° C. The suspension was then stirred for a further hour at −5° C., after which it was heated to 20° C. over three hours and kept at the latter temperature for a further ten hours.

The resulting reaction mixture, a red solution containing a colorless acicular precipitate, was then mixed with 200 ml of water and 500 ml of ether, and worked up in a conventional manner. The solvent-free organic residue, amounting to 76 g, contained, according to gas-chromatographic analysis, 66.9 g of 6-hydroxy-2-cyano-2,5,7,8-tetramethylchromane and 7.6 g of unconverted trimethylhydroquinone.

Recrystallization from acetone/water gave the pure chromane derivative in 81% yield, based on trimethylhydroquinone employed.

The same result was achieved by taking the trimethylhydroquinone suspension, then adding the $BF_3$, and thereafter adding the cyanohydrin.

EXAMPLE 2

Using the method described in the last paragraph of Example 1, but with 0.338 mole of $BF_3$ diethyl-etherate in place of free $BF_3$, 6-hydroxy-2-cyano-2,5,7,8-tetramethylchromane was obtained in 79% yield.

EXAMPLE 3

Using the method described in the last paragraph of Example 1, but with 0.338 mole of tin tetrachloride instead of $BF_3$, the pure chromane derivative was obtained in 75% yield.

EXAMPLE 4

Using the method described in the last paragraph of Example 1, but with anhydrous methylene chloride instead of toluene as the solvent, and with 0.338 mole of aluminum trichloride instead of $BF_3$, 6-hydroxy-2-cyanochromane was obtained in 64% yield.

EXAMPLE 5

Using the method described in the last paragraph of Example 1, but with 0.338 mole of anhydrous zinc chloride instead of $BF_3$, pure 6-hydroxy-2-cyanochromane was obtained in 55% yield, alongside 26% of unconverted trimethylhydroquinone.

EXAMPLE 6

Using the method described in the last paragraph of Example 1, but with 0.338 mole of zinc iodide instead of $BF_3$, 6-hydroxy-2-cyanochromane was obtained in 62% yield. In addition, 20% of unconverted trimethylhydroquinone were isolated.

EXAMPLE 7

15 ml of methylene chloride and 40 ml of nitromethane were added to 45.0 g (0.338 mole) of $AlCl_3$ over 30 minutes at 0° C. The reaction mixture was cooled to −20° C., 25.7 g (0.169 mole) of trimethylhydroquinone and 19.4 g (0.169 mole) of 4-hydroxybutan-2-one cyanohydrin, stabilized with 1 g of phosphoric acid, were then added over 45 minutes, and the mixture was thereafter stirred for 1 hour at −20° C. The temperature was then raised to 25° over 2 hours. After an additional 10 hours' reaction time at 25° C., followed by working up as described in Example 1, pure 6-hydroxy-2-cyanochromane was isolated in 69% yield.

EXAMPLE 8

Using the method described in the last paragraph of Example 1, 23.3 g (0.169 mole) of 2,6-dimethylhydroquinone were reacted with 16.6 g (0.169 mole) of methyl vinyl ketone cyanohydrin, stabilized with 1 g of phosphoric acid, in 125 ml of toluene and 17 ml of nitromethane in the presence of 11.5 g (0.169 mole) of $BF_3$.

Conventional working up gave 6-hydroxy-2,5,7-trimethyl-2-cyanochromane in the form of colorless crystals, in 79% yield; melting point 135° C.

EXAMPLE 9

Using the method described in the last paragraph of Example 1, 57.4 g (0.34 mole) of trimethylhydroquinone were reacted with 19.9 g (0.34 mole) of isopropyl vinyl ketone cyanohydrin, stabilized with 1 g of phosphoric acid, in the presence of 24 g (0.34 mole) of $BF_3$. Conventional working up gave 6-hydroxy-5,7,8-trimethyl-2-isopropyl-2-cyanochromane in the form of colorless crystals, in 77% yield; melting point 132° C.

EXAMPLE 10

Using the method described in the last paragraph of Example 1, but with methylene chloride instead of toluene, 56.0 g (0.338 mole) of tert.-butyl hydroquinone were reacted with 33.6 g (0.338 mole) of methyl vinyl ketone cyanohydrin, which was stabilized with 1 g of phosphoric acid. After chromatography of the crude product over silica gel, using toluene/ethyl acetate, 6-hydroxy-7-tert.-butyl-2-methyl-2-cyanochromane was obtained in 30% yield, as colorless crystals of melting point 153°-155° C.

In addition, 22% of 6-hydroxy-2-methyl-2-cyanochromane were obtained, as colorless crystals of melting point 146°-148° C., due to dealkylation of the tert.-butyl-hydroquinone.

EXAMPLE 11

Using the method described in Example 7, 18.6 g (0.169 mole) of hydroquinone were reacted with 16.6 g (0.169 mole) of methyl vinyl ketone cyanohydrin, which was stabilized with 1 g of phosphoric acid, and 22.4 g (0.169 mole) of $AlCl_3$. After conventional working up of the reaction mixture, analysis by gas chromatography, using toluene/ethyl acetate, showed 22% of 6-hydroxy-2-methyl-2-cyanochromane; colorless crystals of melting point 146°-148° C.

EXAMPLE 12

Using the method described in Example 1, last paragraph, 25.0 g (0.129 mole) of 4-acetoxy-2,3,5-trimethylphenol were reacted with 12.3 g (0.129 mole) of methyl vinyl ketone cyanohydrin, stabilized with phosphoric acid, and with 13.3 g (0.129 mole) of $BF_3$. Conventional working up of the reaction mixture gave, according to analysis by gas chromatography, 25% of 6-acetoxy-2,5,7,8-tetramethyl-2-cyanochromane; colorless crystals, melting point 149°-151° C. In addition, 15% of 6-hydroxy-2,5,7,8-tetramethyl-2-cyanochromane were obtained.

EXAMPLE 13

23.7 g (0.338 mole) of methyl vinyl ketone were added over 5 minutes to a solution of 9.7 g (0.36 mole) of liquid hydrocyanic acid and 34 g of nitromethane whilst stirring, and thereafter 0.5 g of triethylamine was added slowly, first at −20° C. and then at −25° C. The reaction mixture was then kept at −20° C. for 1.5 hours. After acidifying the mixture with 1 g of phosphoric acid, 51.4 g (0.338 mole) of trimethylhydroquinone and 180 g of toluene were added, and 23.0 g (0.338 mole) of $BF_3$ were then passed in over 1.5 hours at −10° C. After stirring for one hour at −5° C., the mixture was brought to room temperature and stirred for 5 hours. Working up by the method described in Example 1 gave pure 2-cyanochromane in 78% yield.

We claim:
1. A process for the preparation of a chromane derivative of the formula I

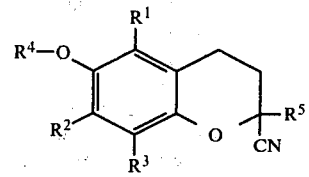

where $R^1$, $R^2$ and $R^3$ are hydrogen or alkyl of 1 to 8 carbon atoms, $R^4$ is hydrogen or alkyl or acyl of 1 to 8 carbon atoms and $R^5$ is alkyl of 1 to 8 carbon atoms, which comprises: reacting a hydroquinone of the formula II

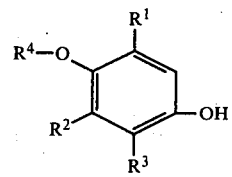

with 10-300 mole %, based on II, of a Lewis acid or of a Lewis acid adduct with a weak Lewis base or of a Lewis acid adduct with a proton acid, and with a nitrile of the formula III

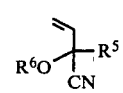

where $R^6$ is hydrogen or acyl or alkyl of 1 to 4 carbon atoms, in the presence of an inert solvent.

2. A process as claimed in claim 1, wherein a nitrile of the formula IIIa

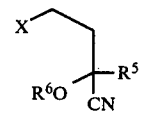

where X is halogen, hydroxyl or alkoxy or acyloxy of 1 to 4 carbon atoms is used to form compound III in situ under the reaction conditions.

3. A process as claimed in claim 1, wherein an equimolar or about equimolar mixture of a cyano compound of the formula IV

Y—CN        IV where Y is hydrogen, one equivalent of a metal cation, or a trialkylsilyl group, and a carbonyl compound IIIb or IIIc

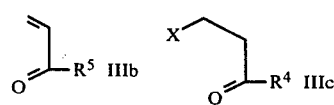

is employed to form compound III in situ under the reaction conditions.

* * * * *